United States Patent [19]
Forbes et al.

[11] Patent Number: 5,079,246
[45] Date of Patent: Jan. 7, 1992

[54] NOVEL INDOLOQUINLONES

[75] Inventors: Ian T. Forbes; Roger T. Martin; Mervyn Thompson, all of Essex, England

[73] Assignee: Beacham Group p. l. c., Brentford, England

[21] Appl. No.: 447,212

[22] Filed: Dec. 7, 1989

[30] Foreign Application Priority Data

Dec. 9, 1988 [GB] United Kingdom ............... 8828806

[51] Int. Cl.$^5$ .................... A61K 31/44; C07D 471/04
[52] U.S. Cl. ................................ 514/232.8; 514/255; 514/285; 544/126; 544/360; 546/15; 546/70; 548/483
[58] Field of Search .................... 546/70, 15; 514/284, 514/285, , 255, 232.8; 548/483; 544/126

[56] References Cited

FOREIGN PATENT DOCUMENTS 245053 12/1987 European Pat. Off. .
249301 12/1987 European Pat. Off. .

Primary Examiner—Mukund J. Shah
Assistant Examiner—E. C. Ward
Attorney, Agent, or Firm—Hopgood, Calimafde, Kalil, Blaustein & Judlowe

[57] ABSTRACT

A compound for formula (I) or a pharmaceutically acceptable salt thereof:

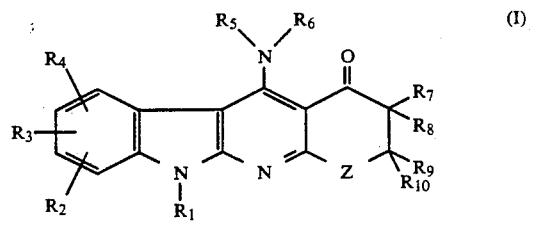

wherein: R1, R2, R3, R4, R5, R6, R7, R8, R9, R10, and Z are described in claim 1.

15 Claims, No Drawings

NOVEL INDOLOQUINLONES

This invention relates to novel compounds having pharmacological activity, to a process for their preparation, to compositions containing them and to their use in the treatment of mammals.

EP-A-0249301 (Beecham Group p.l.c.) describes pyrido[2,3-b]indoles which are useful in the treatment of CNS disorders.

A class of compounds has been discovered, which compounds have been found to have CNS activity, in particular anxiolytic and/or anti-depressant activity.

Accordingly, the present invention provides a compound of formula (I) or a pharmaceutically acceptable salt thereof:

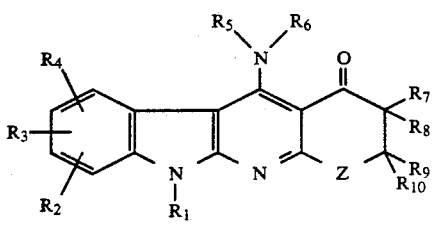

wherein:

$R_1$ is hydrogen, $C_{1-6}$ alkyl, $C_{3-6}$ cycloalkyl, $C_{3-6}$ cycloalkyl-$C_{1-4}$ alkyl, $C_{2-6}$ alkenyl or $C_{2-6}$ alkynyl;

$R_2$, $R_3$ and $R_4$ are independently selected from hydrogen, $C_{1-6}$ alkyl $C_{1-6}$ alkoxy, $C_{1-6}$ alkoxycarbonyl, $C_{1-6}$ alkylthio, hydroxy, $C_{2-7}$ alkanoyl, chloro, fluoro, trifluoromethyl, nitro, amino optionally substituted by one or two $C_{1-6}$ alkyl groups or by $C_{2-7}$ alkanoyl, cyano, carbamoyl and carboxy, and phenyl, phenyl $C_{1-4}$ alkyl or phenyl $C_{1-4}$ alkoxy in which any phenyl moiety is optionally substituted by any of these groups;

$R_5$ and $R_6$ are independently selected from hydrogen, $C_{1-6}$ alkyl, $C_{3-7}$ cycloalkyl, $C_{3-7}$ cycloalkyl-$C_{1-4}$ alkyl, $C_{2-6}$ alkenyl, $C_{1-7}$ alkanoyl, $C_{1-6}$ alkylsulphonyl, di-($C_{1-6}$ alkyl)amino $C_{1-6}$ alkyl, 3-oxobutyl, 3-hydroxybutyl, and phenyl, phenyl $C_{1-4}$ alkyl, benzoyl, phenyl $C_{2-7}$ alkanoyl or benzenesulphonyl any of which phenyl moieties are optionally substituted by one or two halogen, $C_{1-6}$ alkyl, $C_{1-6}$ alkoxy, $CF_3$, amino or carboxy, or $R_5$ and $R_6$ together are $C_{2-6}$ polymethylene optionally interrupted by oxygen or $NR_{11}$ wherein $R_{11}$ is hydrogen or $C_{1-6}$ alkyl optionally substituted by hydroxy;

$R_7$, $R_8$, $R_9$ and $R_{10}$ are independently selected from hydrogen, $C_{1-8}$ alkyl optionally substituted by one or two hydroxy, oxo, $C_{1-4}$ alkoxy, halogen or $CF_3$ groups, $C_{3-7}$ cycloalkyl, $C_{3-7}$ cycloalkyl-$C_{1-4}$ alkyl, $C_{2-7}$ alkanoyl, $C_{2-6}$ alkenyl or $C_{2-6}$ alkynyl either being optionally substituted by one, two or three halogen atoms or $C_{1-4}$ alkyl, $C_{3-7}$ cycloalkenyl optionally substituted by one or two halogen or $C_{1-4}$ alkyl groups, $C_{3-7}$ cycloalkenyl-$C_{1-4}$ alkyl in which the cycloalkenyl ring is optionally substituted by one or two halogen or $C_{1-4}$ alkyl groups, and phenyl optionally substituted by one or two halogen, $C_{1-6}$ alkyl, $C_{1-6}$ alkoxy, $CF_3$, amino or carboxy, or $R_7$ and $R_8$ together and/or $R_9$ and $R_{10}$ together are $C_{3-6}$ polymethylene optionally substituted by $C_{1-6}$ alkyl or $C_{2-6}$ alkenyl; and Z is $(CR_{14}R_{15})_n$ where n is 0, 1 or 2 and $R_{14}$ and $R_{15}$ are independently selected from hydrogen, $C_{1-6}$ alkyl or $C_{2-6}$ alkenyl.

Unless otherwise specified alkyl groups including those in alkoxy, alkenyl and alkynyl moieties within the variables $R_1$ to $R_{15}$ are preferably $C_{1-6}$ alkyl, more preferably $C_{1-3}$ alkyl, such as methyl, ethyl, n- and iso- propyl, and may be straight chain or branched. The term halogen includes fluorine, chlorine, bromine and iodine.

It will be appreciated in selecting variables $R_1$, $R_5$ and $R_6$ that the relevant nitrogen atom is not directly attached to an unsaturated carbon atom.

Values for $R_1$ include hydrogen, methyl, ethyl, n- and iso-propyl, n-, iso-, sec- and tert-butyl, n-, sec-, iso- and neo-pentyl, prop-2-enyl, prop-2-ynyl, cyclopropyl, cyclobutyl, cyclopentyl, cyclopropyl- $C_{1-4}$ alkyl, cyclobutyl-$C_{1-4}$ alkyl and cyclopentyl-$C_{1-4}$ alkyl where values for $C_{1-4}$ alkyl include methylene and ethylene. Preferably $R_1$ is hydrogen, methyl, ethyl, propyl or prop-2-enyl, most preferably methyl.

Values for $R_2$, $R_3$ and $R_4$ include hydrogen, $C_{1-4}$ alkyl, $C_{1-4}$ alkoxy, hydroxy, chloro or phenyl $C_{1-4}$ alkoxy Preferably, two of $R_2$, $R_3$ and $R_4$ represent hydrogen, and more preferably $R_2$, $R_3$ and $R_4$ each represent hydrogen.

Values for $R^5$ and $R^6$ include hydrogen, methyl, ethyl, n- and iso- propyl, n-, sec-, iso- and tert-butyl, n-, sec, iso- and neo-pentyl,cyclopentyl, cyclohexyl, cycloheptyl, cyclopentyl-$C_{1-4}$ alkyl, cyclohexyl-$C_{1-4}$ alkyl and cycloheptyl-$C_{1-4}$ alkyl, where values for $C_{1-4}$ alkyl include methylene and ethylene, but-2-enyl, but-3-enyl,1-methylprop-2-enyl, formyl, acetyl, propionyl, methylsulphonyl, 3-dimethylaminobutyl, 3-oxobutyl, 3-hydroxybutyl, phenyl, benzyl, benzoyl, benzylcarbonyl and benzenesulphonyl, or $R_5$ and $R_6$ together form $C_4$ or $C_5$ polymethylene, $-(CH_2)_2-O-(CH_2)_2-$ or $-(CH_2)_2- NR_{11}-(CH_2)_2-$ where $R_{11}$ is preferably methyl.

Preferably $R_5$ is hydrogen and $R_6$ is hydrogen or $C_{1-6}$ alkyl. More preferably $R_5$ and $R_6$ are hydrogen.

Values for $R_7$ and $R_8$ include hydrogen, methyl, ethyl, n- and iso-propyl, n-, iso-, sec- and tert-butyl, each alkyl moiety being optionally substituted by hydroxy, oxo, $C_{1-4}$ alkoxy or $CF_3$, halogeno-$C_{1-4}$ alkyl, particularly mono- or dihalogeno-$C_{1-4}$ alkyl where the halogen atoms are chlorine or fluorine, prop-2-enyl, prop-2-ynyl, but-2-enyl, but-3-enyl, but-2-ynyl and but-3-ynyl, each alkenyl or alkynyl moiety being optionally substituted by one to three halogen atoms, particularly one or two chlorine atoms or $C_{1-4}$ alkyl, cyclopropyl, cyclobutyl, cyclopentyl and cyclohexyl, cyclopropy-$C_{1-4}$ alkyl, cyclobutyl-$C_{1-4}$ alkyl, cyclopentyl-$C_{1-4}$ alkyl and cyclohexyl-$C_{1-4}$ alkyl, cyclopentenyl, cyclohexenyl, cyclopentenyl-$C_{1-4}$ alkyl and cyclohexenyl-$C_{1-4}$ alkyl, each cycloalkenyl moiety being optionally substituted by one or two halogen or $C_{1-4}$ alkyl groups, or phenyl, or $R_7$ and $R_8$ together form $C_4$ or $C_5$ polymethylene optionally substituted by $C_{1-6}$ alkyl or $C_{2-6}$ alkenyl.

Preferably $R_7$ is hydrogen, $C_{1-6}$ alkyl or $C_{2-6}$ alkynyl and $R_8$ is hydrogen or $C_{1-6}$ alkyl. More preferably $R_7$ is hydrogen, methyl or ethyl and $R_8$ is hydrogen or methyl.

Values for $R_9$ and $R_{10}$ include those listed above for $R_7$ and $R_8$, in particular hydrogen, methyl, ethyl, n- and iso-propyl, n-, iso-, sec- and t-butyl, prop-2-enyl, but-3-enyl and phenyl. Preferably $R_9$ is hydrogen or methyl and $R_{10}$ is hydrogen, methyl or phenyl.

Where n is one or two, values for $R_{14}$ and $R_{15}$ include hydrogen, methyl, ethyl, n- and iso- propyl, n-, iso-, sec- and t-butyl, prop-2-enyl and but-3-enyl. Preferably $R_{14}$ is hydrogen and $R_{15}$ is hydrogen or methyl. More preferably $R_{14}$ and $R_{15}$ are hydrogen.

Preferably n is 1 or 2. More preferably n is 1.

There is a favoured group of compounds within formula (I) of formula (II) or a pharmaceutically acceptable salt thereof:

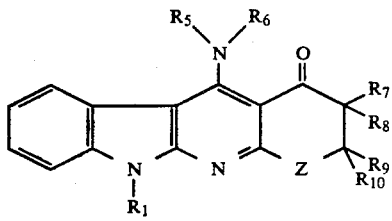
(II)

wherein $R_1$, $R_5$, $R_6$, $R_7$, $R_8$, $R_9$, and Z are defined in formula (I).

Preferred values for $R_1$, $R_5$, $R_6$, $R_7$, $R_8$, $R_9$, $R_{10}$, $R_{14}$ and $R_{15}$ are as described under formula (I).

There is a preferred group of compounds within formula (II) of formula (III) or a pharmaceutically acceptable salt thereof:

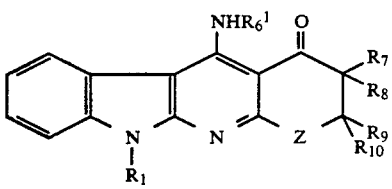
(III)

wherein $R_6^1$ is hydrogen or $C_{1-6}$ alkyl and $R_1$, $R_7$, $R_8$, $R_9$, $R_{10}$ and Z are as defined in formula (I).

Preferred values for $R_1$, $R_7$, $R_8$, $R_9$, $R_{10}$, $R_{14}$ and $R_{15}$ are as described for the corresponding variables in formula (I).

$R_6^1$ is preferably hydrogen.

The compounds of the formula (I) can form acid addition salts with acids, such as the conventional pharmaceutically acceptable acids, for example, maleic, hydrochloric, hydrobromic, phosphoric, acetic, fumaric, salicylic, citric, lactic, mandelic, tartaric and methanesulphonic.

It will be appreciated that the compounds of formula (I) in which $R_1$, $R_5$ or $R_6$ is hydrogen may exist tautomerically in more than one form. The invention extends to each of these forms and to mixtures thereof.

Compounds of the formula (I) may exist in the form of optical and geometric isomers. The present invention comprises all such optical and geometric isomers and mixtures thereof including racemates.

Compounds of formula (I) may also form solvates such as hydrates, and the invention also extends to these forms. When referred to herein, it is understood that the term "compound of formula (I)" also includes solvates thereof.

The present invention also provides a process for the preparation of a compound of formula (I), or a pharmaceutically acceptable salt thereof, which process comprises the condensation of a compound of formula (IV):

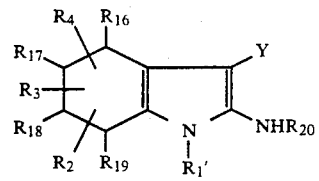
(IV)

with a compound of formula (V):

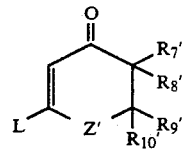
(V)

wherein $R_1'$ is $R_1$ as defined in formula (I) or an N-protecting group, $R_2$, $R_3$ and $R_4$ are as defined in formula (I), $R_{16}$, $R_{17}$, $R_{18}$ and $R_{19}$ are each hydrogen or $R_{16}$ and $R_{17}$, and $R_{18}$ and $R_{19}$ together represent a bond, L is a leaving group, Y is a group CN or $COL_1$, wherein $L_1$ is a leaving group, $R_{20}$ is hydrogen or an N-protecting group and $R_7'$, $R_8'$, $R_9'$, $R_{10}'$ and $Z'$ are $R_7$, $R_8$, $R_9$, $R_{10}$ and Z respectively, as defined in formula (I) or a group convertible to $R_7$, $R_8$, $R_9$, $R_{10}$ and Z, respectively, to give an acyclic enamine intermediate of formula (VI):

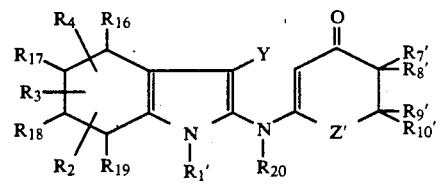
(VI)

wherein Y, $R_1'$, $R_2$, $R_3$, $R_4$, $R_{16}$, $R_{17}$, $R_{18}$, $R_{19}$ and $R_{20}$ are as defined in formula (IV) and $R_7'$, $R_8'$, $R_9'$, $R_{10}'$ and $Z'$ are as defined in formula (V); and thereafter, optionally or as necessary, and in any appropriate order, cyclising the enamine intermediate, separating any enantiomers, converting $R_{20}$ when hydrogen to an N-protecting group, converting $R_7'$, $R_8'$, $R_9'$, $R_{10}'$ and $Z'$ to $R_7$, $R_8$, $R_9$, $R_{10}$ and Z, respectively, when Y is a group $COL_1$, converting the resulting hydroxy group to a leaving group and reacting the latter with a compound $HNR_5R_6$, removing any $R_1'$ N-protecting group, removing any $R_{20}$ N-protecting group, converting $R_{16}$, $R_{17}$, $R_{18}$ and $R_{19}$ when hydrogen to two bonds, interconverting $R_1$, $R_2$, $R_3$, $R_4$, $R_5$, $R_6$, $R_7$, $R_8$, $R_9$, $R_{10}$ or Z and/or forming a pharmaceutically acceptable salt of the compound of formula (I).

Suitable examples of the leaving group L include halogens, such as chloro and bromo, hydroxy, $C_{1-6}$ acyloxy such as acetoxy or $C_{1-6}$ alkoxy, such as methoxy or ethoxy, preferably hydroxy. When L is hydroxy, it will be appreciated that the compound of formula (V) exists in more than one tautomeric form.

Intermediates of formula (VI), and salts thereof which can be optionally isolated before cyclisation, are novel and form an aspect of this invention.

The condensation step may be carried out under conditions conventional for condensation reactions, at elevated temperatures in an inert solvent such as toluene or benzene in the presence of a catalyst such as para-toluene-sulphonic acid, with water separation.

The cyclisation of the enamine intermediate of formula (VI) may also be carried out under conventional conditions, in the presence of a strong base such as an alkali metal alkoxide, for example sodium methoxide in a suitable solvent such as methanol, at elevated temperature, or in the presence of a Lewis acid such as zinc chloride, copper (I) acetate or tin (IV) chloride in a suitable solvent such as n-butyl acetate at elevated temperatures. Lewis acid catalysed cyclisation using copper (I) acetate or tin (IV) chloride is preferred.

It should be appreciated that for the cyclisation of a compound of formula (VI) $R_{20}$ is preferably hydrogen.

Conversion of $R_{16}$, $R_{17}$, $R_{18}$ and $R_{19}$ when hydrogen to two bonds may be carried out under conventional aromatisation conditions, with an oxidising agent such as 2,3-dichloro-5,6-dicyano-1,4-benzoquinone, in an inert solvent such as benzene or toluene.

Alternatively, the conversion may be carried out by catalytic dehydrogenation using a conventional metal catalyst such as Pd/C in a suitable solvent such as xylene or mesitylene at elevated temperature, for example 100°–180° C., or by sulphur dehydrogenation under conventional conditions.

In the compound of formula (IV), it is preferred that $R_{16}$ and $R_{17}$, and $R_{18}$ and $R_{19}$ together represent a bond.

Suitable examples of $R_1'$ N-protecting groups include benzyl, mono- or di-methoxybenzyl, which may be removed conventionally, for example by heating with $AlCl_3$ in benzene, or by treatment with trifluoroacetic acid and anisole, optionally in the presence of sulphuric acid and optionally with heating.

Conversion of $R_1$ hydrogen to $R_1$ alkyl, alkenyl or alkynyl may be carried out by treatment of the NH compound with a strong base, such as sodium hydride in dimethyl formamide, followed by reaction with the appropriate alkyl, alkenyl or alkynyl halide, preferably the iodide or bromide.

Suitable examples of a leaving group $L_1$ when Y is $COL_1$, include hydroxy and alkoxy, such as ethoxy or methoxy, more preferably methoxy. In such cases the reaction of the compounds of formulae (IV) and (V) gives a resulting compound having an hydroxy group in the 4-position of the pyridine ring. The hydroxy group may be converted to a leaving group such as those defined above for L, preferably halo such as chloro, by reaction with a halogenating agent such as phosphorus oxychloride or phosphorus oxybromide. The leaving group may be displaced by the compound $HNR_5R_6$ under conventional conditions for nucleophilic aromatic displacements, at elevated temperatures in an inert solvent such as toluene, methanol, ethanol, pyridine, dimethyl formamide or dioxan. Alternatively, the reaction may be carried out in neat $HNR_5R_6$ which functions as the solvent.

Conversion of $R_5$ and $R_6$ hydrogen to other $R_5/R_6$ may be carried out in accordance with conventional procedures for the alkylation or acylation of a primary amine. Acylation may be carried out by reaction with the appropriate acyl halide. However, $R_5/R_6$ other than hydrogen or acyl groups are preferably introduced via the route in which Y is $COL_1$ in the compound of formula (IV), by displacement of the leaving group with the compound $HNR_5R_6$ as discussed above.

Interconversion of $R_2$, $R_3$ and $R_4$ may be carried out by conventional procedures for the conversion of aromatic substituents. Thus, for example, a chloro substituent may be introduced by direct chlorination using standard conditions, such as chlorine in chloroform.

Examples of group $Z'$ include $(CR_{14}'R_{15}')_n$ where n is as previously defined and $R_{14}'$ and $R_{15}'$ are $R_{14}$ and $R_{15}$ or groups convertible thereto.

Conversions of $R_7'$, $R_8'$ and $R_{14}'$ and $R_{15}'$ in $Z'$ (n in $Z'$ is 1 or 2), wherein $R_7'$, $R_8'$, $R_{14}'$ and $R_{15}'$ are $R_7$, $R_8$, $R_{14}$ and $R_{15}$ respectively, as defined in formula (I) or groups convertible thereto, may be carried out by the reaction of a corresponding compound wherein $R_7'$, $R_8'$, $R_{14}'$ or $R_{15}'$ is hydrogen with two equivalents of lithium diisopropylamide mono (tetrahydrofuran) at low temperatures in a suitable solvent such as tetrahydrofuran. The resulting enolate anion is treated with a molar equivalent of an $R_7'$-, $R_8'$-, $R_{14}'$- or $R_{15}'$- halogen compound, as desired, for example iodomethane or iodoethane, to give the corresponding compound in which $R_7'$ and/or $R_8'$ and/or $R_{14}'$ and/or $R_{15}'$ is other than hydrogen. The procedure may be repeated to achieve disubstitution.

Reaction of the enolate anion with an $\alpha,\omega$-dihaloalkane may be carried out to give the corresponding compound of formula (I) in which $R_7$ and $R_8$ together are polymethylene, as described by G. Stork et al., J. Amer. Chem. Soc., 1973, 95, 3414–5.

It should be appreciated that where the conversion is carried out on a compound of formula (VI), it may be necessary in some circumstances to have $R_{20}$ as a N-protecting group to prevent reaction of the $R_7'$-, $R_8'$-, $R_{14}'$-, or $R_{15}'$- halogen compound with the secondary amine function and also to direct substitution to Z.

Suitable examples of $R_{20}$ N-protecting groups include trimethylsilyl and 2-(trimethylsilyl)ethoxymethyl, which may be removed conventionally, for example using t-butylammonium fluoride in an inert solvent.

If $R_7'$, and $R_8'$ are hydrogen and preferential conversion of $R_{14}'$ and $R_{15}'$ is desired, it is necessary to first of all protect $R_7'$ and $R_8'$. An example of a suitable protecting group is trimethylsilyl.

Preferential conversion of $R_{14}'$ and $R_{15}'$ in $Z'$ (n in $Z'$ is 1 or 2) in compounds of formula (VI) may alternatively be carried out as described by P. S. Mariano et al J. Org. Chem. 1981, 46, 4643–54, by reacting a compound of formula (VI) in which $R_{14}'$ and $R_{15}'$ are hydrogen with 2 moles of potassium or lithium bis(trimethylsilyl)amide at low temperatures in an inert solvent such as tetrahydrofuran. The resulting $\gamma$-enolate anion is treated as described above to introduce the required groups $R_{14}'$ and $R_{15}'$.

An example of a group $R_7'$, $R_8'$ $R_9'$, $R_{10}'$, $R_{14}'$ or $R_{15}'$ convertible to $R_7$, $R_8$, $R_9$, $R_{10}$, $R_{14}$ or $R_{15}$ respectively, is an alkylthiomethyl group, which can afford $R_7$, $R_8$, $R_9$, $R_{10}$, $R_{14}$ or $R_{15}$ respectively, as a methyl group by reductive desulphurisation, for example using Raney Nickel. Separation into enantiomers maybe carried out, if desired, by first oxidising the alkylthiomethyl group to the chiral sulphoxide as described by H. B. Kagan et al., J. Amer. Chem. Soc. 1984, 106, 8188 or H. B. Kagan et al., Nouv. J. Chim. 1985, 9, 1, followed by physical separation of the diastereoisomers (for example by fractional crystallisation or chromatography). Reductive desulphurisation will afford the single enantiomer.

Conversions of $R_9'$ and $R_{10}'$ hydrogen when n in Z is O may be carried out by a procedure analogous to that described above for $R_{14}'$ and $R_{15}'$.

Pharmaceutically acceptable salts may be prepared conventionally by reaction with the appropriate acid or derivative.

A class of intermediates obtained by the reaction of certain compounds of formula (IV) with certain compounds of formula (V) comprises compounds of formula (VII) or a salt, thereof:

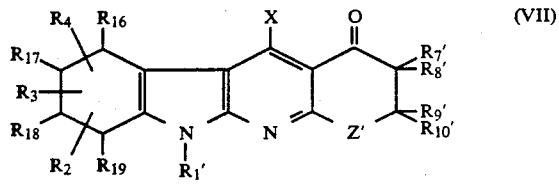

wherein X is $NH_2$, OH or chloro, $R_1'$, $R_2$, $R_3$, $R_4$, $R_{16}$, $R_{17}$, $R_{18}$ and $R_{19}$ are as defined in formula (IV), and $R_7'$, $R_8'$, $R_9'$, $R_{10}'$ and $Z'$ are as defined in formula (V) with the proviso that when $R_1'$, $R_7'$, $R_8'$, $R_9'$, $R_{10}'$, and $Z'$ are $R_1$, $R_7$, $R_8$, $R_9$, $R_{10}$ and $Z$ as defined in formula (I) and $R_{16}$ and $R_{17}$, and $R_{18}$ and $R_{19}$ together represent a bond, X is not $NH_2$.

Intermediates of formula (VII) are novel and form an aspect of this invention.

Compounds of formulae (IV) and (v) are known or can be prepared by analogous processes to those used for preparing known compounds. Thus, for example, the compounds of formula (IV) where $R_{16}$, $R_{17}$, $R_{18}$ and $R_{19}$ are each hydrogen may be prepared by the reaction of a compound of formula (VIII):

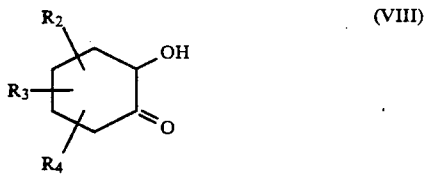

with $CH_2(CN)_2$ and an alkylamine such as methylamine or an aralkylamine such as 4-methoxybenzylamine or benzylamine by a procedure analogous to that described by H. J. Roth et al., Arch.Pharmaz., 1975, 308. 179.

Alternatively, the compound of formula (VIII) may be reacted with $NCCH_2CO_2C(CH_3)_3$ and an alkylamine such as methylamine or an aralkylamine such as benzylamine by a procedure analogous to that described by H. J. Roth et al., Arch.Pharmaz., 1975, 308, 179. This gives a compound of formula (IV) in which Y is $COL_1$ and $L_1$ is t-butoxy, which may be converted to other $L_1$ by conventional procedures.

Compounds of formula (IV) where $R_{16}$, $R_{17}$, $R_{18}$ and $R_{19}$ together form two bonds may be prepared by procedures conventional in indole chemistry.

Thus, for example, a compound of formula (IX):

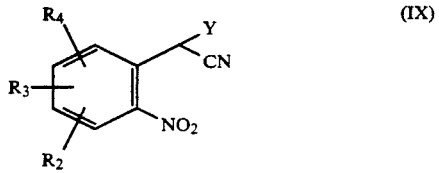

wherein $R_2$, $R_3$ and $R_4$ are as defined in formula (I) and Y is as defined in formula (IV), may be reduced and cyclised by treatment with a metal such as zinc, iron or tin in an acid such as acetic acid, in an inert solvent such as toluene at elevated temperature by a procedure analogous to that described by K. L. Munshi et al J. Het. Chem. 1977, 14, 1145. Alternatively, when Y is CN the reduction and cyclisation may be effected by treatment with aqueous sodium dithionite by a procedure analogous to that described in EP 0107963 (Example 1). This procedure gives a compound of formula (IV) in which $R_1'$ is hydrogen and which may be N-substituted under conventional conditions as described above to give other compounds of formula (IV).

Compounds of formula (IX) are known or may be prepared by procedures analogous to those for preparing known compounds.

Compounds of the formula (V) where $R_7'$ and $R_8'$ are hydrogen, $Z'$ is a methylene radical and L is hydroxy may be prepared by reaction of a compound of formula (X):

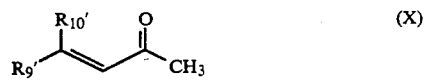

with a malonic ester compound, for example dimethyl- or diethylmalonate, followed by cyclisation, hydrolysis and decarboxylation. Compounds of the formula (X) may be prepared by known methods, for example by reaction of a saturated aliphatic aldehyde with acetone at elevated temperatures in the presence of an acid or basic catalyst.

The above procedure may be adapted to give compounds of the formula (V) where $R_7'$ is other than hydrogen by use of a malonic ester compound in which the methylene radical is substituted by $R_7'$, where $R_7'$ is other than hydrogen.

Alternatively, compounds of formula (V) in which L is hydroxy, for example optionally substituted 1,3-cyclopentanediones, 1,3-cyclohexanediones and 1,3-cycloheptanediones may be prepared via epoxidation of the corresponding cyclopent-2-en-1-one, cyclohex-2-en-1-one and cyclohept-2-en-1-one compounds with hydrogen peroxide under basic conditions as described in Organic Synthesis, Coll. Vol. (IV), 552–3, (1963), and subsequent ring opening using catalytic quantities of tetrakis-(triphenylphosphine)palladium(O) and 1,2-bis(-diphenylphosphino)ethane as described in J. Amer. Chem. Soc. 1980, 102, 2095–6.

Compounds of formula (V) in which L is hydroxy or $C_{1-6}$ alkoxy, $R_7'$ and/or $R_8'$ are other than hydrogen and $R_9'$, $R_{10}'$ and $Z'$ are as defined for formula (V) may be prepared from compounds of formula (V) in which L is hydroxy and $R_7'$ and/or $R_8'$ are hydrogen as described by G. Stork et al., J. Org. Chem., (1973) 38, 1775–6. Treatment with a $C_{1-6}$ alkyl alcohol to give an intermediate in which L is $C_{1-6}$ alkoxy is followed by reaction with an equivalent of lithium diisopropylamide mono (tetrahydrofuran) at low temperatures in a suitable solvent such as tetrahydrofuran. The resulting enolate anion is treated with a molar equivalent of an $R_7'$- or $R_8'$-halogen compound or with an $\alpha,\omega$-dihaloalkane by an analogous procedure to that described above for the conversion of $R_7'$ and $R_8'$ in the process of the invention, including separation into enantiomers, if desired. The procedure may be repeated to achieve disubstitution. Where $Z'$ is a bond, simultaneous interconversion of $R_7'$ or $R_8'$ hydrogen and $R_9'$ or $R_{10}'$ hydrogen may be achieved by treatment with two equivalents of lithium di-isopropylamide and subsequent reaction with excess halogen derivative as described by M. Koreeda et al., J. Chem. Soc. Chemical Communications, (1979) 449-50. Conversion to L hydroxy may be effected by acid hydrolysis.

Alternatively, compounds of formula (V) in which L is hydroxy and $R_7'$, $R_8'$, $R_9'$, $R_{10}'$ and $Z'$ are as defined for formula (V), may be prepared by the reaction of an ester of an $\alpha,\beta$ unsaturated carboxylic acid with a substituted or unsubstituted propan-2-one as disclosed in GB 1485610 (Hoechst).

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, is usually adapted for oral or parenteral administration and, as such, may be in the form of tablets, capsules, oral liquid preparations, powders, granules, lozenges, reconstitutable powders, or injectable or infusable solutions or suspensions. Orally administrable compositions are generally preferred.

Tablets and capsules for oral administration may be in unit dose form, and may contain conventional excipients, such as binding agents, fillers, tableting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The invention also provides a compound of formula (I) or a pharmaceutically acceptable salt thereof, for pharmaceutical use. By pharmaceutical use is meant for use as an active therapeutic substance in the treatment or prophylaxis of disorders in mammals including humans. Compounds of formula (I) and their pharmaceutically acceptable salts are of particular use in the treatment of CNS disorders, in particular anxiety or depression.

The invention further provides a method of treatment of CNS disorders, in particular anxiety or depression in mammals including humans, which comprises administering to the sufferer a therapeutically effective amount of a compound of formula (I) or a pharmaceutically acceptable salt thereof.

The invention also provides the use of a compound of formula (I) or a pharmaceutically acceptable salt thereof in the manufacture of a medicament for the treatment of CNS disorders, in particular anxiety or depression in mammals including humans.

The dose of the compound used in the treatment of CNS disorders, such as anxiety or depression will vary in the usual way with the seriousness of the disorders, the weight of the sufferer, and other similar factors However, as a general guide suitable unit doses may be 0.05 to 1000 mg, more suitably 0.05 to 20.0 mg, for example 0.2 to 10 mg; and such unit doses may be administered more than once a day, for example two or three a day, so that the total daily dosage is in the range of about 0.01 to 100 mg/kg; and such therapy may extend for a number of weeks or months.

Within the above indicated dosage range, no adverse toxicological effects are indicated with the compounds of the invention.

The following Examples illustrate the preparation of the compounds of the invention. The following Descriptions illustrate the preparation of intermediates to the compounds of the present invention.

DESCRIPTION 1

1-(4-Methoxyphenyl)methyl-2-[(3-oxo-1-cyclohexen-1-yl)amino]-4,5,6,7-tetrahydro-1H-indole-3-carbonitrile (D1)

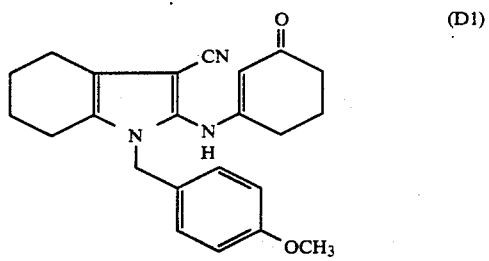

A solution of 2-amino-1-(4-methoxyphenyl)methyl-4,5,6,7-tetrahydro-1H-indole-3-carbonitrile (prepared by the method described in EP-0249301A, Description 5) (22.4 g; 79.7 mM), 1,3-cyclohexanedione (9.3 g; 79.7 mM) and para toluenesulphonic acid (2 g; 10.5 mM) in toluene (350 ml) was vigorously refluxed with distillation until no more water distilled over (ca. 1h). The solution was cooled and poured onto water (500 ml). The toluene layer was separated, and the aqueous layer extracted with dichloromethane ($\times 2$). The combined organic phase was washed with saturated aqueous sodium hydrogen carbonate, dried ($Na_2SO_4$) and evaporated to dryness to afford a pale yellow solid. Crystallisation from ethyl acetate afforded the title compound (D1)(24.7 g; 82%) as a pale yellow solid.

m.p. 143-5°

NMR (CDCl₃) δ: 1.70-1.88 (4H, m), 1.92-2.10 (2H, m), 2.25-2.45 (6H, m), 2.45-2.60 (2H, m), 3.80 (3H, s), 4.78 (2H, s), 5.06 (1H, s), 6.15 (1H, broad s), 6.78-6.96 (4H, m).

DESCRIPTION 2

2-(5,5-Dimethyl-3-oxo-1-cyclohexen-1-yl)amino]-1-(4-methoxyphenyl)methyl-4,5,6,7-tetrahydro-1H-indole-3-carbonitrile (D2)

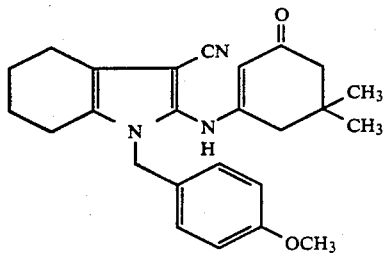

The title compound (D2) was prepared from 5,5-dimethyl-1,3-cyclohexanedione in 78% yield using a procedure similar to that described in Description 1. Product was obtained as a buff coloured solid.

NMR (CDCl₃) δ: 1.06 (6H, s), 1.66-1.87 (4H, m), 2.18 (2H, s), 2.24 (2H, s), 2.30-2.45 (2H, m), 2.45-2.60 (2H, m), 3.78 (3H, s), 4.77 (2H, s), 5.05 (1H, s), 6.08 (1H, broad s), 6.77-6.95 (4H, m).

DESCRIPTION 3

2-Amino-1-methyl-1H-indole-3-carbonitrile (D3)

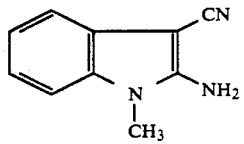

To a solution of 2-amino-1H-indole-3-carbonitrile (produced by a method analogous to that disclosed in EP 0107963 example 1) (20.0 g 12.7 mM) in DMF (100 ml) at ca. 5° and under an atmosphere of nitrogen, was added potassium tert-butoxide (14.59 g, 12.7 mmol) portionwise over 5 minutes. The cooling bath was removed and the whole stirred at room temperature for 30 minutes. The whole was then recooled and methyl iodide (8 ml, 12.7 mM), dissolved in DMF (20 ml), added dropwise such that the temperature remained below 5°. After a further 40 minutes at this temperature, water (500 ml) was added dropwise and the resulting solid collected by filtration, washed with water and dried under reduced pressure to give the title compound (D3) (13.08 g, 60%) as a brown solid.

NMR (D₆DMSO) δ: 3.63 (3H, s), 7.00-7.20 (4H, m), 7.21-7.40 (2H, m).

DESCRIPTION 4

(±) 2-[(5-Methyl-3-oxo-1-cyclohexen-1-yl)amino]-1-methyl-1H-indole-3-carbonitrile (D4)

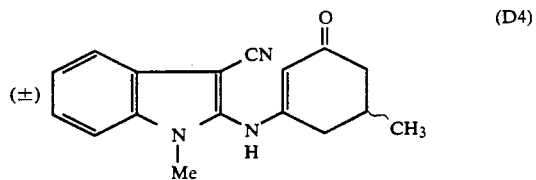

The title compound (D4) was prepared from intermediate D3 and 5-methyl-1,3-cyclohexanedione in 69% yield using a procedure similar to that described in Description 1. Product was obtained as a pale yellow solid. m.p. 235-6°.

NMR (D₆DMSO) δ: 1.29 (3H, d, J=7.5 Hz), 2.04-2.84 (5H, m), 3.78 (3H, s), 4.99 (1H, s), 7.30-7.55 (2H, m), 7.64-7.85 (2H, m).

DESCRIPTION 5

11-Amino-6-(4-methoxyphenyl)methyl-1,2,3,4,7,8,9,10-octahydro-6H-quinindolin-1-one (D5)

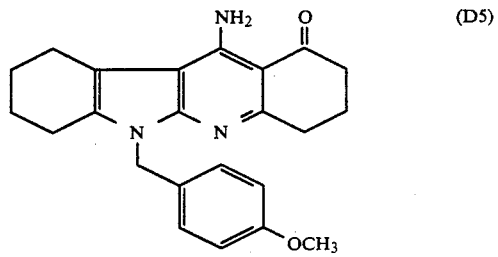

Method A

A suspension of intermediate D1 (0.5 g; 1.33 mM) copper (1) acetate (0.043 g; 0.33 mM) in n-butyl acetate (10 ml) was heated to reflux whereupon a solution resulted. After refluxing for 10 minutes, the whole was cooled and poured onto 5M ammonium hydroxide solution (20 ml). The whole was shaken with dichloromethane (20 ml), the organic layer separated, and the aqueous layer further extracted with dichloromethane (×2). The combined organic phase was washed with water and brine, dried (Na₂SO₄) and evaporated to afford a crude solid (0.5 g). Crystallisation from methanol gave the title compound (D5) (0.40 g; 80%) as a pale yellow solid. m.p. 146-7°.

NMR (CDCl₃) δ: 1.70-1.90 (4H, m), 2.00-2.17 (2H, m), 2.40-2.53 (2H, m), 2.59-2.70 (2H, m), 2.82-2.96 (2H, m), 2.96-3.09 (2H, m), 3.78 (3H, s), 5.26 (2H, s), 6 80 (2H, d, J=8 Hz), 7.05 (2H, d, J=8 Hz).

Method B

A solution of 2-amino-1-(4-methoxyphenyl)methyl-4,5,6,7-tetrahydro-1H-indole-3-carbonitrile (prepared by the method described in EP-0249301A, Description 5) (20.0 g; 71 mM), 1,3-cyclohexanedione (8.3 g; 71 mM) and para toluenesulphonic acid (0.5 g; 2.6 mM) in toluene (280 ml) was vigorously refluxed with distillation until no more water distilled over. The solution was cooled and n-butyl acetate (280 ml) and tin (IV) chloride (0.83 ml; 7.1 mM) were added. The solution was then refluxed for 10 minutes and allowed to cool. The reaction mixture was poured onto 1% aqueous sodium hydroxide solution (500 ml) and shaken with dichloromethane (200 ml). The organic layer was separated, and the aqueous layer further extracted with dichloromethane (×2). The combined organic phase was washed with water and brine, dried (Na₂SO₄) and evaporated to dryness to afford a crude solid. The crude solid was flash chromatographed on t.l.c. alumina with dichloromethane elution, followed by crystallisation from methanol to give the title compound (D5) (21.2 g; 79%) as a pale yellow solid in two crops.

m.p. 146.5–7°.

NMR (CDCl₃) δ: 1.70–1.90 (4H, m), 2 00–2.17 (2H, m), 2.40–2.53 (2H, m), 2.59–2.70 (2H, m), 2.82–2.96 (2H, m), 2.96–3.09 (2H, m), 3.78 (3H, s), 5.26 (2H, s), 6.80 (2H, d, J=8 Hz), 7.05 (2H, d, J=8 Hz).

DESCRIPTION 6

11-Amino-3.3-dimethyl-6-(4-methoxyphenyl)methyl-1,2,3,4,7,8,9,10-octahydro-6H-quinindolin-1-one (D6)

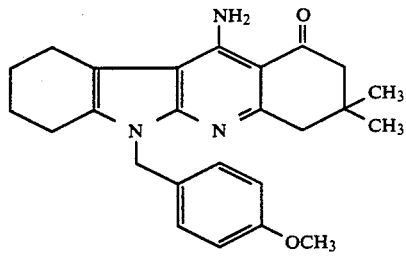
(D6)

A suspension of intermediate D2 (10.0 g; 24.8 mM) tin (IV) chloride (0.3 ml; 2.48 mM) in n-butyl acetate (100 ml) was heated to reflux. After refluxing for 10 minutes, the whole was cooled and poured onto 2.5M sodium hydroxide solution (200 ml). The whole was shaken with dichloromethane (200 ml), the organic layer separated, and the aqueous layer further extracted with dichloromethane (×2). The combined organic phase was washed with water and brine, dried (Na₂SO₄) and evaporated to afford a crude solid (10.0 g). Crystallisation from methanol gave the title compound (D6) (9.29 g; 93%) as an off-white solid.

NMR (CDCl₃) δ: 1.10 (6H, s), 1.65–1.92 (4H, m), 2.32–2.59 (4H, m), 2.89 (4H, s), 3.75 (3H, s), 5.27 (2H, s), 6.70–6.90 (2H, m), 6.96–7.13 (2H, m).

DESCRIPTION 7

(±) 11-Amino-6-(4-methoxyphenyl)methyl-1,2,3,4,7,8,9,10-octahydro-3-phenyl-6H-quinindolin-1-one (D7)

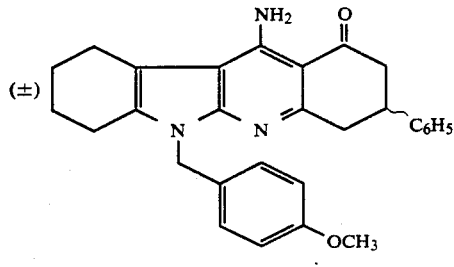
(D7)

The title compound (D7) was prepared from 5-phenyl-1,3-cyclohexanedione in 78% yield using a procedure similar to that described in Description 5 (Method B). Product was obtained as an off white solid. m.p. 168–170°.

NMR (CDCl₃) δ: 1.65–1.93 (4H, m), 2.40–2.57 (2H, m), 2.79–3.01 (4H, m), 3.15–3.39 (2H, m), 3.39–3.57 (1H, m), 3.78 (3H, s), 5.28 (2H, s), 6.75–6.87 (2H, m), 7.00–7.14 (2H, m), 7.15–7.45 (5H, m).

DESCRIPTION 8

11-Amino-6-(4-methoxyphenyl)methyl-1,2,3,4-tetrahydro-6H-quinindolin-1-one (D8)

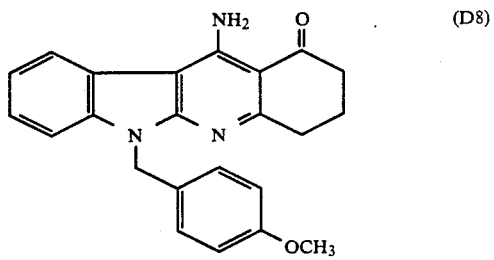
(D8)

The title compound (D8) was prepared from the intermediate D5 in 72% yield using a procedure similar to that described in EP-0249301A (Description 7) by treatment with 2,3-dichloro-5,6-dicyano-1,4-benzoquinone in toluene. Product was obtained as an off-white solid.

m.p. 194–7°.

NMR (CDCl₃) δ: 2.06–2.23 (2H, m), 2.64–2.79 (2H, m), 3.08–3.20 (2H, m), 3.76 (3H, s), 5.59 (2H, s), 6.80 (2H, d, J=8 Hz), 7.18 (2H, d, J=8 Hz), 7.23–7.40 (3H, m), 7.81 (1H, d, J=8 Hz).

DESCRIPTION 9

11-Amino-3,3-dimethyl-6-(4-methoxyphenyl)methyl-1,2,3,4-tetrahydro-6H-quinindolin-1-one (D9)

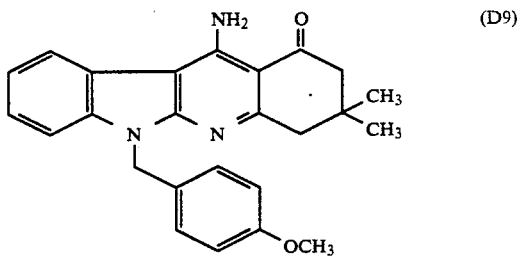
(D9)

The title compound (D9) was prepared from the intermediate D6 in 77% yield using a procedure similar to that described in Description 8. Product was obtained as an off-white solid.

NMR (CDCl₃) δ: 1.15 (6H, s), 2.58 (2H, s), 3.00 (2H, s), 3.75 (3H, s), 5.59 (2H, s), 6.74–6.82 (2H, m), 7.10–7.38 (5H, m), 7.74–7.83 (1H, m).

DESCRIPTION 10

(±)
11-Amino-6-(4-methoxyphenyl)methyl-3-phenyl-1,2,3,4-tetrahydro-6H-quinindolin-1-one (D10)

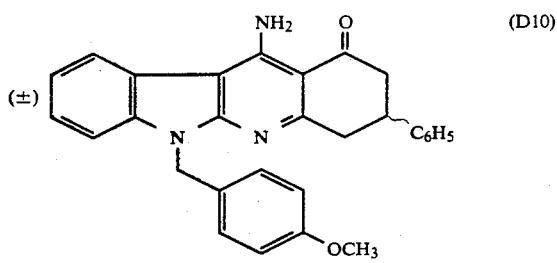

The title compound (D10) was prepared from the intermediate D7 in 71% yield using a procedure similar to that described in Description 8. Product was obtained as a pale yellow solid. m.p. 163-5°.

NMR (CDCl$_3$/D$_6$DMSO) δ: 2.85-3.00 (2H, m), 3.25-3.44 (2H, m), 3.44-3.63 (1H, m), 3.70 (3H, s), 5.57 (2H, s), 6.70-6.85 (2H, m), 7.11-7.45 (10H, m), 8.10-8.22 (1H, m).

DESCRIPTION 11

(±) 4-Methyl-1,3-cyclohexanedione (D11)

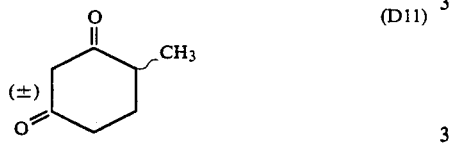

To a stirred solution of lithium diisopropylamide mono (tetrahydrofuran) (100 ml, 150 mM, 1.5M solution) in dry tetrahydrofuran (100 ml) under an atmosphere of nitrogen and at −78° C. was added dropwise 3-ethoxy-2-cyclohexen-1-one (21.0 g, 150 mM) dissolved in tetrahydrofuran (70 ml) over a period of 15 min. After an additional 45 min, methyl iodide (21.29 g, 150 mM) dissolved in dry tetrahydrofuran (10 ml) was added dropwise over a period of 5 min. After a further 15 min the cooling bath was removed and the whole stirred at room temperature for 1 h. Water was then added and the enol ether intermediate recovered into ether, washed (brine), dried (Na$_2$SO$_4$) and evaporated to dryness. The oil thus obtained was dissolved in ethanol (100 ml) and 5N hydrochloric acid (228 ml) added. The whole was stirred at room temperature for 45 min. Water (800 ml) was added, the aqueous phase made basic to pH 8-9 (NaOH) and extracted with ethyl acetate. The aqueous phase was re-acidified (HCl) and the product extracted into ethyl acetate. The organic phase was washed with brine, dried (Na$_2$SO$_4$) and evaporated to give the title compound (D11) (17.6 g) (92%) as an oil. Product could be used directly in the preparation of intermediate D13 without further purification.

The product could also be purified by distillation (bp 108-110°/1.5 mmHg lit 110°/1 mmHg (G. L. Burge D. J. Collins and J. D. Reitz, Aust. J. Chem., 1982, 35, 1913)

NMR (CDCl$_3$) δ: 1.22 (3H, d, J=7 Hz), 1.45-1.73 (1H, m), 1.95-2.28 (1H, m), 2.34-2.83 (3H, m), 3.32-3.58 (m, keto form), 4.19 (broad s, OH, enol form, variable with concentration), 5.5 (s, enol form)

DESCRIPTION 12

(±) 4-Ethyl-1,3-cyclohexanedione (D12)

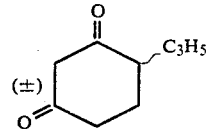

The title compound (D12) was prepared from 3-ethoxy-2-cyclohexen-1-one and ethyl iodide using a procedure similar to that described in Description 11. Product was used in the preparation of D14 without further purification.

DESCRIPTION 13

(±)
2-[(4-Methyl-3-oxo-1-cyclohexen-1-yl)amino]-1-methyl-1H-indole-3-carbonitrile (D13)

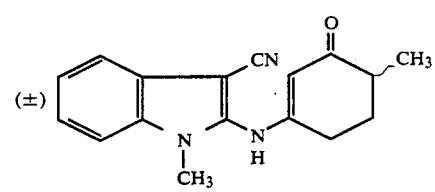

The title compound (D13) was prepared from intermediates D3 and D11 in 61% yield using a procedure similar to that described in Description 1.

m.p. 194-5°.(ethyl acetate).

NMR (CDCl$_3$) δ: 1.15 (3H, d, J=11 Hz), 1.68-1.95 (1H, m), 2.02-2.20 (1H, m , 2.23-2.43 (1H, m), 2.50-2.80 (2H, m), 3.59 (3H, s), 4.99 (1H, s), 7.10-7.50 (4H, m), 7.58-7.69 (1 H, m)

DESCRIPTION 14

(±)
2-[(4-Ethyl-3-oxo-1-cyclohexen-1-yl)amino]-1-methyl-1H-indole-3-carbonitrile (D14)

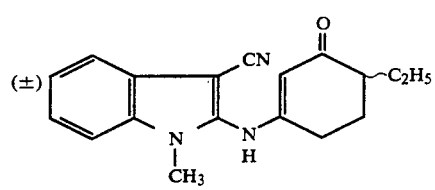

The title compound (D14) was prepared from the intermediates D3 and D12 in 61% yield using a procedure similar to that described in Description 1. Product was purified by flash chromatography on t.l.c. silica with dichloromethane/ethyl acetate elution.

m.p 205-6° (methanol)

NMR (CDCl$_3$) δ: 0.94 (3H, t, J=8.5 Hz), 1.30-1.58 (1 H, m), 1.71-1.99 (2H, m), 2.05-2.28 (2H, m), 2.57-2.77 (2H, m), 3.60 (3H, s), 5.02 (1H, s), 7.17-7.49 (4H, m), 7.55-7.71 (1H, m)

DESCRIPTION 15

2-(4,4-Dimethyl-3-oxo-1-cyclohexen-1-yl)amino]1-methyl-1H-indole-3-carbonitrile (D15)

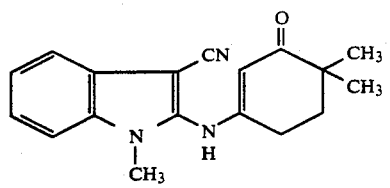

The title compound (D15) was prepared from the intermediate D3 and 4,4-dimethyl-1,3-cyclohexanedione (K. Katsuura, K. Yamaguchi, S. Sakai and K. Mitsuhashi, Chem. Pharm. Bull, 1983, 31, 1518) in 86% yield using a procedure similar to that described in Description 1.

NMR (CDCl$_3$) δ: 0.83 (6H, s), 1.60 (2H, t, J=6 Hz), 2.39 (2H, t, J=6 Hz), 3.31 (3H, s), 4.59 (1H, s), 6.88–7.12 (3H, m), 7.28–7.38 (1H, m), 8.76 (1H, broad s).

DESCRIPTION 16

1-Methyl-2-[(3-oxo-1-cyclopenten-1-yl)amino]-1H-indole-3-carbonitrile (D16)

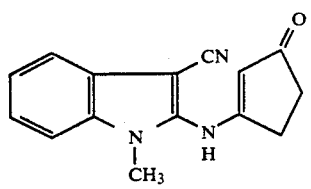

The title compound (D16) was prepared from intermediate D3 and 1,3-cyclopropanedione in 61% yield using a procedure similar to that described in Description 1. Product was obtained as a solid.

NMR (D$_6$DMSO) δ: 2.23–2.47 (2H, m), 2.74–2.93 (2H, m), 3.71 (3H, s), 5.09 (1H, m), 7.20–7.45 (2H, m), 7.51–7.72 (2H, m), 10.22 (1H, broad s).

DESCRIPTION 17

1-Methyl-2-[(3-oxo-1-cyclohecten-1-yl)amino]1H-indole-3carbonitrile (D17)

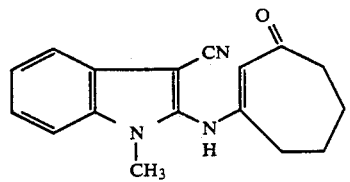

The title compound (D17) was obtained during the preparation of compound E16 as described in Example 16.

NMR (D$_6$ DMSO) δ: 1.76–2.10 (4H, m), 2.48–2.65 (2H, m), 2.70–2.94 (2H, m), 3.62 (3H, s), 4.91 (1H, s), 7.12–7.50 (3H, m), 7.53–7.68 (1H, m), 8.80–9.09 (1H, broad s).

DESCRIPTION 18

1-Methyl-2-[(3-oxo-1-cyclohexen-1-yl)amino]-1H-indole-3-carbonitrile (D18)

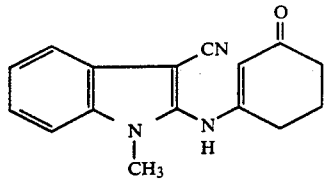

The title compound (D18) was prepared from intermediate D3 and 1,3-cyclohexanedione in 60% yield using a procedure similar to that described in Description 1. The product was recrystallised from ethyl acetate.

M.p. 239–41°.

NMR (CDCl$_3$) δ: 2.02–2.19 (2H, m), 2.30–2.46 (2H, m), 2.55—2.70 (2H, m), 3.63 (3H, s), 5.04 (1H, s), 6.64 (1H, broad s), 7.22–7.42 (3H, m), 7.60–7.75 (1H,m).

EXAMPLE 1

11-Amino-1,2,3,4-tetrahydro-6H-quinindolin-1-one (E1)

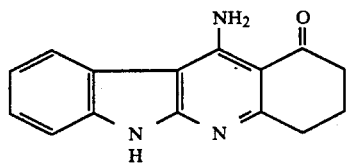

The title compound (E1) was prepared from the intermediate D8 in 91% yield using a procedure similar to that described in EP 0249301A (Example 1, alternative procedure) by treatment with anisole, trifluoroacetic acid and concentrated sulphuric acid at room temperature. Product was obtained as a white solid.

m.p.>300°

NMR (D$_6$DMSO) δ: 2.05–2.20 (2H, m), 2.67–2.78 (2H, m), 3.04–3.17 (2H, m), 7.28–7.60 (3H, m plus 1H broad s), 8.40 (1H, d, J=8 HZ), 9.50–9.89 (1H broad s), 11.93 (1H, s).

Found: C, 71.50; H, 5.45; N, 16.39%. C$_{15}$H$_{13}$N$_3$O requires: C, 71.70; H, 5.21; N, 16.72%.

EXAMPLE 2

11-Amino-3,3-dimethyl-1,2,3,4-tetrahydro-6H-quinindolin-1-one (E2)

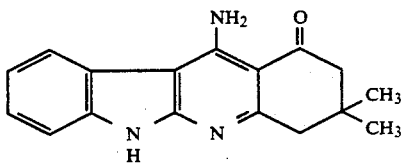

The title compound (E2) was prepared from the intermediate D9 using a procedure similar to that described in EP 0249301A (Example 1, alternative procedure) by treatment with anisole, trifluoroacetic acid and concentrated sulphuric acid at room temperature. Product was obtained as a solid.

NMR (D$_6$DMSP) δ: 1.20 (6H, s), 2.60 (2H, s), 3.06 (2H, s), 7.25–7.90 (3H, m plus 1H, broad s), 8.38–8.53 (1H, m), 9.50–10.05 (1H, broad s), 12.30 (1H, s).

EXAMPLE 3

(±)11-Amino-3-phenyl-1,2,3,4-tetrahydro-6H-quinindolin-1-one (E3)

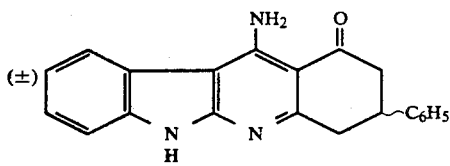

The title compound (E3) was prepared from the intermediate D10 in 95% using a procedure similar to that described in Example 1. An analytical sample was obtained by boiling the solid in methanol, collecting the solid and drying in vacuo. m.p. >300°.

NMR (D$_6$DMSO) δ: 2.77–2.93 (1H, m), 2.99–3.72 (4H, m), 7.20–7.70 (9H, m), 8.38–8.51 (1H, m), 9.46–9.88 (1H, broad s), 12.03 (1H, s).

Found: C, 76.68; H, 5.25; N, 12.86%.

C$_{21}$H$_{17}$N$_3$O requires: C, 77.04; H, 5.23; N, 12.84%.

EXAMPLE 4

11-Amino-6-methyl-1,2,3,4-tetrahydro-6H-quinindolin-1-one (E4)

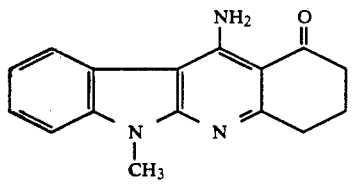

A suspension of compound E1 (8.48 g, 32 mM) in dry dimethylformamide (95 ml) was added dropwise to a stirred suspension of 80% sodium hydride (35.2 mM) in dimethylformamide (35 ml) at 0° under N$_2$. After ½h, methyl iodide (5.33 g, 37.5 mM) was added dropwise, and the solution allowed to stir at room temperature for approximately 16 h. The solution was then poured onto water and extracted twice with dichloromethane. The combined organic phase was washed well with water, dried (Na$_2$SO$_4$) and evaporated to give a solid (9.71 g). Recrystallization from methanol afforded the title compound (E4) (6.08 g; 68%) as an off white solid. m.p. 145–6°.

NMR (CDCl$_3$) 2.06–2.23 (2H, m), 2.63–2.80 (2H, m), 3.05–3.19 (2H, m), 3.90 (3H, s), 7.20–7.51 (3H, m), 7.80 (1H, d, J=8 Hz).

Found: C, 72.32; H, 5.82; N, 15.74%.

C$_{16}$H$_{15}$N$_3$O requires: C, 72,43; H, 5.70; N, 15.84%.

Alternatively, example E4 can be prepared using intermediate D18 using a procedure similar to that described in Description 5.

EXAMPLE 5

11-Amino-6-ethyl-1,2,3,4-tetrahydro-6H-quinindolin-1-one (E5)

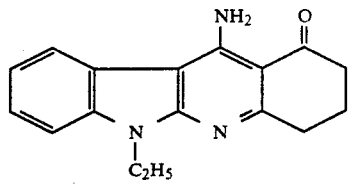

The title compound (E5) was prepared from compound E1 and ethyl iodide in 66% using a procedure similar to that described in Example 4. Product was obtained as a white solid. m.p. 178–9°.

NMR (CDCl$_3$) δ: 1.42 (3H, t, J=7.5 Hz), 2.02–2.26 (2H, m), 2.58–2.80 (2H, m), 3.00–3.23 (2H, m), 4.49 (2H, q, J=7.5 Hz), 7.20–7.53 (3H, m), 7.70–7.90 (1H, m).

Found: C, 73.51; H, 6.44; N, 15.07%.

C$_{17}$H$_{17}$N$_3$O requires: C, 73.10; H, 6.13; N, 15.04%.

EXAMPLE 6

11-Amino-6-n-propyl-1,2,3,4-tetrahydro-6H-quinindolin-1-one (E6)

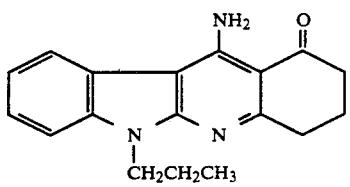

The title compound (E6) was prepared from compound and 1-iodopropane in 39% yield using a procedure similar to that described in Example 4. Product was obtained as a white solid. m.p. 148–9°.

NMR (CDCl$_3$) δ: 0.98 (3H, t, J=7.5 Hz), 1.74–2.02 (2H, m), 2.05–2.27 (2H, m), 2.56–2.80 (2H, m), 3.01–3.22 (2H, m), 4.36 (2H, t, J=7.5 Hz), 7.18–7.55 (3H, m), 7.73–7.90 (1H, m).

Found: C, 73.81; H, 6.61; N, 14.29%.

C$_{18}$H$_{19}$N$_3$O requires: C, 73.69; H, 6.53; N, 14.32%.

EXAMPLE 7

11-Amino-6-(2-propenyl)-1,2,3,4-tetrahydro-6H-quinindolin-1-one (E7)

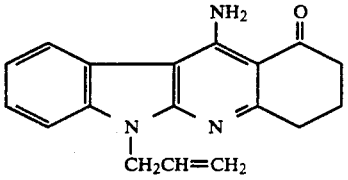

The title compound (E7) was prepared from compound E1 and 3-bromopropene in 42% yield using a procedure similar to that described in Example 4. Product was obtained as a white solid. m.p. 132–3°.

NMR (CDCl$_3$ δ: 2.04–2.27 (2H, m), 2.56–2.80 (2H, m), 2.96–3.23 (2H, m), 4.90–5.30 (4H, m), 5.89–6.15 (1H, m), 7.20–7.50 (3H, m), 7.70–7.90 (1H, m).

Found: C, 74.01; H, 5.72; N, 14.28%.

C$_{18}$H$_{17}$N$_3$O requires: C, 74.20; H, 5.88; N, 14.42%.

EXAMPLE 8

11-Amino-1,2,3,4-tetrahydro-3,3,6-trimethyl-6H-quinindolin-1-one (E8)

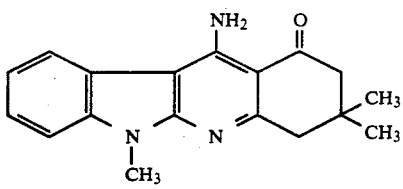

The title compound (E8) was prepared from compound E2 in 44% using a procedure similar to that described in Example 4. Product was obtained as a white solid.

m.p. 198-200°.

NMR (CDCl$_3$) δ: 1.13 (6H, s , 2 57 (2H, s), 3.00 (2H, s), 3.90 (3H, s), 7.21-7.50 (3H, m), 7.76-7.87 (1H, m).

Found: C, 73.80; H, 6.87; N, 14.07%.

C$_{18}$H$_{19}$N$_3$O requires: C, 73.69; H, 6.53; N, 14.32%.

EXAMPLE 9

(±)
11-Amino-6-methyl-3-phenyl-1,2,3,4-tetrahydro-6H-quinindolin-1-one (E9)

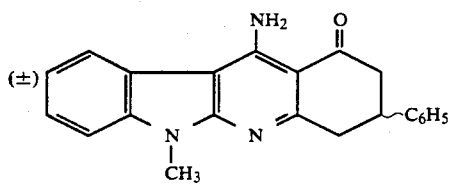

The title compound (E9) was prepared from compound E3 in 50% yield using a procedure similar to that described in Example 4. Product was obtained as a white solid. m.p. 205-6°.

NMR (CDCl$_3$) δ: 2.87-3.08 (2H, m), 3.26-3.65 (3H, m), 3.92 (3H, s), 7.21-7.55 (8H, m), 7.80-7.90 (1H, m).

Found: C, 77.21; H, 5.53; N, 12.32%.

C$_{22}$H$_{19}$N$_3$O requires: C, 77.40; H, 5.61; N, 12.31%.

EXAMPLE 10

(±)
11-Amino-3,6-dimethyl-1,2,3,4-tetrahydro-6H-quinindolin-1-one (E10)

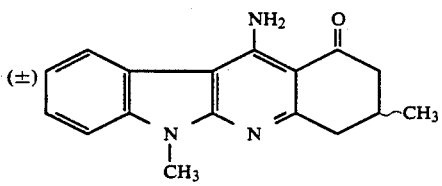

The title compound (E10) was prepared from the intermediate D4 in 34.5% yield using a procedure similar to that described in Description 5 (Method A). Product was obtained as a white solid. m.p. 216-7°.

NMR (CDCl$_3$) δ: 1.09-1.24 (3H, m), 2.21-2.47 (2H, m), 2.50-3.30 (3H, m), 3.89 (3H, s), 7.20-7.32 (1H, m), 7 32-7.50 (2H, m), 8.09-8.21 (1H, m).

Found: C, 73.35; H, 6.28; N, 15.05%.

C$_{17}$H$_{17}$N$_3$O requires: C, 73.10; H, 6.13; N, 15.04%.

EXAMPLE 11

(±)
11-Amino-2,6-dimethyl-1,2,3,4-tetrahydro-6H-quinindolin-1-one (E11)

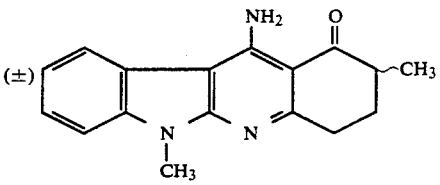

Method A

The title compound (E11) was prepared from the intermediate D13 in 41% yield using a procedure similar to that described in Description 6. Product was obtained as an off white solid m.p. 155-6.5°. The product could also be purified via preparation of the tartrate salt followed by liberation of the free base.

NMR (CDCl$_3$) δ: 1.31 (3H, d, J=11 Hz), 1.80-2.03 (1H, m), 2.11-2.30 (1H, m), 2.55-2.78 (1H, m), 3.04-3.31 (2H, m), 3.90 (3H, s), 7.21-7.53 (3H, m), 7.73-7.89 (1H, m)

found: C, 73.16; H, 6.14; N, 15.02%.

C$_{17}$H$_{17}$N$_3$O requires: C, 73.10; H, 6.13; N, 15.04%.

The racemic mixture obtained was separated into the two enantiomers by the use of analytical H.P.L.C. using the following conditions:

Column: Chiral-A.G.P. 4.0×100 mm; ID=18RC

Eluent: 20/80 CH$_3$OH/0.02M aqueous phosphate buffer at pH 7.0.

Flow: 1.0 ml/min.

Detection: U.V. at 278 nm.

The retention times of the enantiomers under these conditions were 34.0 and 42.2 minutes respectively.

Method B

To a solution of the compound E4 (0.50 g, 1.88 mM) in dry tetrahydrofuran (17 ml) at −78° and under an atmosphere of nitrogen, was added lithium diisopropylamide mono (tetrahydrofuran) (3 ml, 3.8 mM, 1.5M solution) over a period of 10 minutes. The whole was stirred at −78° for an additional 45 minutes before methyl iodide (0.12 ml, 1.88 mM) was added. The whole was held at this temperature for an additional 1 h before the cooling bath was removed. After an additional 30 minutes water (30 ml) was added and product was extracted into dichloromethane (3×50 ml). The organic phase was washed with brine (50 ml), dried (Na$_2$SO$_4$) and evaporated to dryness to give the title compound (E11) (0.47 g 89%) which was in the preparation of E15 without further purification.

NMR (CDCl$_3$) δ: 1.31 (3H, d, J=11 Hz), 1.80-2.01 (1H,m), 2.11-2.30 (1H, m), 2.54-2.77 (1H, m), 3.05-3.30 (2H, m), 3.89 (3H, s), 7.20-7.52 (3H, m), 7.72-7.88 (1H, m).

EXAMPLE 12

(±)
11-Amino-2-ethyl-6-methyl-1,2,3,4-tetrahydro-6H-quinindolin-1-one (E12)

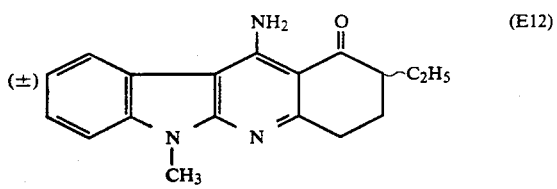

The title compound (E12) was prepared from the intermediate D14 in 66% yield using a procedure similar to that described in Description 6. Product was obtained as a buff coloured solid.

m.p. 129-131° (ethyl acetate-petroleum ether (60-80)).

NMR (CDCl$_3$) δ: 1.06 (3H, t, J=7 Hz), 1.50-1.75 (1H, m), 1.80-2.13 (2H, m), 2.16-2.35 (1H, m), 2.38-2.57 (1H, m), 2.98-3.33 (2H, m), 3.89 (3H, s), 7.21-7.50 (3H, m), 7.71-7.88 (1H, m)

Found: C, 73.87; H, 6.72; N, 14.09%.
C$_{18}$H$_{19}$N$_3$O requires: C, 73.69; H, 6.53; N, 14.32%.

EXAMPLE 13

11-Amino-1,2,3,4-tetrahydro-2,2,6-trimethyl-6H-quinindolin-1-one (E13)

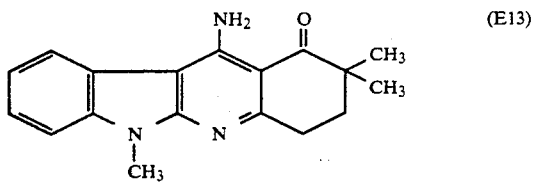

The title compound (E13) was prepared from the intermediate D15 in 53% yield using a procedure similar to that described in Description 6. Crystallisation from methanol gave the title compound (E13) 53% as a buff coloured solid.

m.p. 188-9°
NMR (CDCl$_3$) δ: 1.29 (6H, s), 2.00 (2H, t, J=6 Hz), 3.19 (2H, J=6 Hz), 3.89 (3H, s), 7.21-7.35 (1H, m), 7.36-7.52 (2H, m), 7.72-7.87 (1H, m).

Found: C, 73.61; H, 6.59; N, 14.36%.
C$_{18}$H$_{19}$N$_3$O requires: C, 76.69; H, 6.53; N, 14.32%.

EXAMPLE 14

(±)
11-Amino-6-methyl-2-(2-propynyl)-1,2,3,4-tetrahydro-6H-quinindolin-1-one (E14)

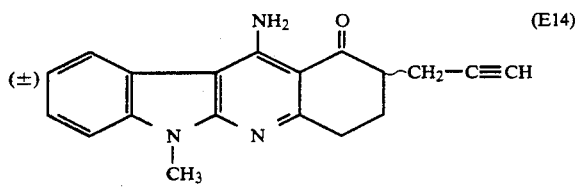

The title compound (E14) was prepared from the compound E4 and propargyl bromide in 55% yield using a procedure similar to that described in Example 11 (Method B). Product was obtained as an off white solid (CH$_3$OH).

NMR (CDCl$_3$) δ: 2.00-2.30 (2H, m), 2.46-2.73 (2H, m), 2.73-2.90 (1H, m), 2.92-3.11 (1H, m), 3.11-3.42 (2H, m), 3.97 (3H, s), 7.32-7.60 (3H, m), 7.80-7.95 (1H, m)

EXAMPLE 15

(±)
11-Amino-1,2,3,4-tetrahydro-2,4,6-trimethyl-6H-quinindolin-1-one (E15)

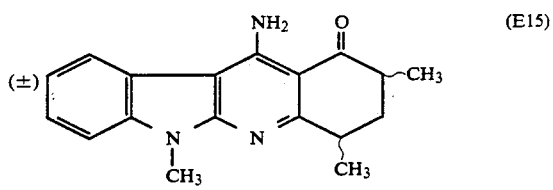

To a solution of compound E11, (method B) (0.47 g, 1.68 mM) in dry tetrahydrofuran (20 ml) under an atmosphere of nitrogen and at −78° was added dropwise lithium diisopropylamide mono(tetrahydrofuran) (2.6 ml, 3.7 mM, 1.5 M solution) over a period of 5 minutes. The whole was then stirred at −78° for a further 30 minutes followed by −40° for 30 minutes. After re-cooling to −78°, methyl iodide (0.1 ml, 1.68 mM) in dry THF (5 ml) was added dropwise over 2 minutes. The whole was stirred at this temperature for an additional 10 minutes, before the cooling bath was removed and the whole allowed to warm to room temperature. Water (50 ml) was then added and the product extracted into dichloromethane (3×50 ml). The organic phase was washed with brine (50 ml), dried (Na$_2$SO$_4$) and evaporated to dryness to give a crude product (0.50 g). Product was purified by flash chromatography on t.l.c. silica with petroleum ether (60-80)/ethyl acetate elution to give the title compound (E15) (0.22 g, 44%) Rf 0.47 (SiO$_2$, 30% ethyl acetate, 70% petroleum ether (60-80)) which was converted to the tartrate salt (0.18g). m.p. 206-11° (ethanol).

NMR (D$_6$DMSO) δ: 1.19 (3H, d, J=7 Hz), 1.41 (3H, d, J=7 Hz), 1.81-2.09 (2H, m), 2.69-2.91 (1H, m), 3.05-3.28 (1H, m), 3.81 (3H, s), 4.31 (tartrate), 7.05-7.47 (2H, m, plus 1H broad singlet), 7.48-7.62 (1H, m), 8.23-8.39 (1H, m), 9.68 (1H, broad s).

MS measured 293.1537, calculated for C$_{18}$H$_{19}$N$_3$O 293.1528.

EXAMPLE 16

12-Amino-7-methyl-cyclohepta[5,6]pyrido[2,3-b]indol-1-one (E16)

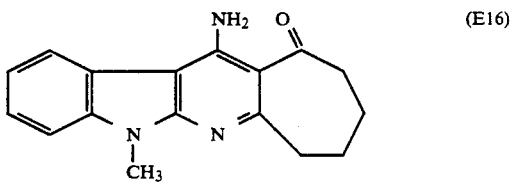

To a solution of the intermediate D3 (32.2 mM) and para-toluenesulphonic acid (0.53 g, 2.78 mM) in toluene (200 ml), heated under vigorous reflux with water removal, was added dropwise over a period of ½ h, 1,3-cycloheptadione (3.01 g, 23.9 mM) (CA, 101, 151464j) dissolved in toluene (50 ml). After an additional ¾ h the solution was allowed to cool and poured onto saturated aqueous sodium bicarbonate solution. The toluene layer was separated and the aqueous layer extracted with ethyl acetate containing ca. 5% methanol (×3). The combined organic phase was washed with saturated brine, dried (Na$_2$SO$_4$) and evaporated to dryness to afford a brown oil containing a mixture of compounds. Chromatography (SiO$_2$, dichloromethane/ethyl acetate) afforded the title compound (E16) (1.78 g, 27%) Rf 0.57 (SiO$_2$ 2:1 dichloromethane:ethyl acetate) as a pale yellow solid m.p. 124°-6° C. (ethyl acetate-petroleum ether 60-80).

Also isolated by chromatography was [(3-oxo-1-cyclohepten-1-yl)amino]-1-methyl-1H-indole -3-carbonitrile (D17) (1.30 g, 20%) Rf 0.19 (SiO$_2$, 2:1 dichloromethane:ethyl acetate). This intermediate could be converted to the title compound (E16) using a procedure similar to that described in Description 6.

NMR (CDCl$_3$) δ: 1.77-2.10 (4H, m), 2.78-2.94 (2H, m), 3.12-3.30 (2H, m), 3.92 (3H, s), 6.90-7.60 (5H, m), 7.77-7.90 (1H, m).

EXAMPLE 17

10-Amino-5-methyl-cyclopenta[5,6]pyrido[2,3-b]indol-1-one (E17)

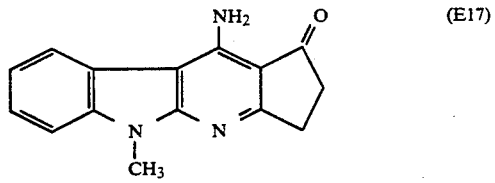

The title compound (E17) was prepared from the intermediate D16 in 60% yield using a procedure similar to that described in Description 6. Product was obtained as a pale green solid. m.p. 279-80°.

NMR (CDCl$_3$) δ: 2.67-2.84 (2H, m), 3.07-3.25 (2H, m), 3.91 (3H, s), 6.10-7.15 (2H, broad s), 7.20-7.56 (3H, m), 7.72-7.88 (1H, m).

Found: C, 71.72; H, 5.47; N, 16.68%.

C$_{15}$H$_{13}$N$_3$O requires: C, 71.70; H, 5.21; N, 16.72%.

EXAMPLE 18

(±)12-Amino-2,7-dimethyl-cyclohepta[5,6]pyrido[2,3-b]-indol-1-one (E18)

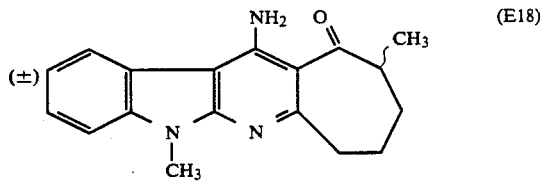

The title compound (E18) was prepared from compound E16 using a procedure similar to that described in Example (Method B).

MS measured 293.1526, calculated for C$_{18}$H$_{19}$N$_3$O 293.1528.

PHARMACOLOGICAL DATA

Geller-Seifter Procedure

Potential anxiolytic properties have been evaluated using the Geller-Seifter procedure based on that originally described by Geller and Seifter (1960) Psychopharmacologia, 1, 482-492. This procedure has been shown to be selective for drugs with anxiolytic properties (Cook and Sepinwall (1975) 'Mechanism of Action of Benzodiazepines' ed. Costa, E. and Greengard, P., Raven Press, New York, pp. 1-28).

Rats are trained on a variable interval 30 sec schedule (VI30) to press a lever in order to obtain food reward. The 3 min sessions of the VI30 schedule alternate with 3 min of a schedule (FR5) in which every 5th lever press is followed by a presentation of a food pellet paired with a 0.2 sec mild footshock. The amplitude of the shock is adjusted for each rat to give equivalent response rates. The total study consists of VI and FR components and lasts 30 mins. Rats typically respond with high rates of lever pressing under the VI30 schedule and low response rats under the FR5 'conflict' session. Anxiolytic drugs increase the suppressed response rates of rats in 'conflict' sessions.

The compound is administered intraperitoneally or orally to groups of 6-16 rats 30 min (intraperitoneal route) or 60 min (oral route) before testing.

The results are expressed as the percentage increase in square root of the total number of lever presses in the FR5 'conflict' sessions. Square root transformation is necessary to normalise the data for statistical analysis using parametric methods. A change in the square root of the VI can indicate non-specific drug effects i.e. stimulation or sedation.

Testing Results

The following compounds have shown activity in the above tests as detailed in the Table 1.

TABLE 1

| Compound | Dose mg/kg | increase in resonding in the 'conflict' session |
|---|---|---|
| E1 | 20 p.o. | +16% |
| E4 | 20 p.o. | +29% |
| E5 | 20 p.o. | +29% |
| E6 | 20 p.o. | +17% |
| E7 | 20 p.o. | +16% |
| E10 | 20 p.o. | +17% |
| E11 | 20 p.o. | +52% |
| E12 | 20 p.o. | +33% |
| E13 | 20 p.o. | +21% |
| E16 | 20 p.o. | +11% |
| E17 | 100 p.o. | +37% |

[$^{35}$S]-TBPS binding to rat cerebral cortex membranes in vitro

[$^{35}$S]-TBPS labels a site on or near the Cl$^-$ channel portion of the GABA$_A$/BDZ/Cl$^-$ channel complex. Literature studies have shown that [$^{35}$S]-TBPS binding is directly related to the permeability of the Cl$^-$ channel (e.g. Concas et al, 1988). Anxiolytic agents such as benzodiazepines and barbiturates allosterically inhibit the binding, whilst anxiogenic agents (e.g. benzodiazepine inverse agonists) potentiate the binding.

Modulation of [$^{35}$S]-TBPS binding is measured by a method similar to that of Gee et al (1986).

Pooled rat cerebral cortices were homogenised in 20 volumes of 0.32M sucrose and centrifuged at 1000 g for 20 minutes (4° C.). The supernatant was removed and recentrifuged at 50,000 g (4° C., 20 mins). The P$_2$ pellet was then suspended in 20 volumes of Tris citrate buffer (pH 7.1) and centrifuged at 50,000 g (4° C., 20 mins). This washing step was repeated three times and the pellet finally resuspended in 20 volumes of buffer and stored at −70° C. prior to use.

The tissue suspension (50 μl) was incubated (25° C., 120 mins) with [$^{35}$S]-TBPS (2 nM) in Tris citrate buffer (pH 7.1) containing 0.2M NaCl and 5×10$^{-6}$M GABA. Non-specific binding was measured in the presence of 10$^{-4}$M picrotoxin. Varying concentrations of test drugs 10$^{-7}$, 10$^{-6}$, 10$^{-5}$ and 10$^{-4}$M final concentration) were added in a volume of 50 μl. The total assay volume was 500 μl. Incubation was stopped by rapid filtration using a Skatron cell harvester and radioactivity measured by liquid scintillation spectrometry. IC$_{50}$'s were calculated as the concentration of test drug to inhibit 50% of specific binding. Concas A. et al, (1988) J. Neurochem. 51(6), 1868–1876. Gee K. W. et al, (1986) Mol. Pharmacol. 30, 218–225.

The results are shown in Table 2.

TABLE 2

| Compound | [$^{35}$S]-TBPS IC$_{50}$ μM |
|---|---|
| E5 | 7.5+ |
| E6 | 3.8+ |
| E7 | 1.9* |
| E8 | 4.4+ |
| E11 | 1.2* (n = 2) |
| E12 | 1.4* |
| E13 | 1.7* (n = 2) |
| E14 | 1.0* |
| E15 | 3.8* (n = 2) |
| E16 | 3.3* |

*done in the presence of GABA
+done in the absence of GABA

We claim:

1. A compound of formula (I) or a pharmaceutically acceptable salt thereof:

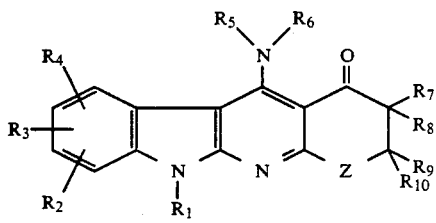

wherein:
R$_1$ is hydrogen, C$_{1-6}$ alkyl, C$_{3-6}$ cycloalkyl, C$_{3-6}$ cycloalkyl-C$_{1-4}$ alkyl, C$_{2-6}$ alkenyl or C$_{2-6}$ alkynyl;
R$_2$, R$_3$ and R$_4$ are independently selected from hydrogen, C$_{1-6}$ alkyl, C$_{1-6}$ alkoxy, C$_{1-6}$ alkoxycarbonyl, C$_{1-6}$ alkylthio, hydroxy, C$_{2-7}$ alkanoyl, chloro, fluoro, trifluoromethyl, nitro, amino optionally substituted by one or two C$_{1-6}$ alkyl groups or by C$_{2-7}$ alkanoyl, cyano, carbamoyl and carboxy, and phenyl, phenyl C$_{1-4}$ alkyl or phenyl C$_{1-4}$ alkoxy in which any phenyl moiety is optionally substituted by any of these groups;
R$_5$ and R$_6$ are independently selected from hydrogen, C$_{1-6}$ alkyl, C$_{3-7}$ cycloalkyl, C$_{3-7}$ cycloalkyl-C$_{1-4}$ alkyl, C$_{2-6}$ alkenyl, C$_{1-7}$ alkanoyl, C$_{1-6}$ alkylsulphonyl, di-(C$_{1-6}$ alkyl)amino C$_{1-6}$ alkyl, 3-oxobutyl, 3-hydroxybutyl, and phenyl, phenyl C$_{1-4}$ alkyl benzoyl, phenyl C$_{2-7}$ alkanoyl or benzenesulphonyl any of which phenyl moieties are optionally substituted by one or two halogen, C$_{1-6}$ alkyl, C$_{1-6}$ alkoxy, CF$_3$, amino or carboxy, or R$_5$ and R$_6$ together are C$_{2-6}$ polymethylene optionally interrupted by oxygen or NR$_{11}$ wherein R$_{11}$ is hydrogen or C$_{1-6}$ alkyl optionally substituted by hydroxy;

R$_7$, R$_8$, R$_9$ and R$_{10}$ are independently selected from hydrogen, C$_{1-8}$ alkyl optionally substituted by one or two hydroxy, oxo, C$_{1-4}$ alkoxy, halogen or CF$_3$ groups, C$_{3-7}$ cycloalkyl, C$_{3-7}$ cycloalkyl-C$_{1-4}$ alkyl, C$_{2-7}$ alkanoyl, C$_{2-6}$ alkenyl or C$_{2-6}$ alkynyl either being optionally substituted by one, two or three halogen atoms or C$_{1-4}$ alkyl, C$_{3-7}$ cycloalkenyl optionally substituted by one or two halogen or C$_{1-4}$ alkyl groups, C$_{3-7}$ cycloalkenyl-C$_{1-4}$ alkyl in which the cycloalkenyl ring is optionally substituted by one or two halogen or C$_{1-4}$ alkyl groups, and phenyl optionally substituted by one or two halogen, C$_{1-6}$ alkyl, C$_{1-6}$ alkoxy, CF$_3$, amino or carboxy, or R$_7$ and R$_8$ together and/or R$_9$ and R$_{10}$ together are C$_{3-6}$ polymethylene optionally substituted by C$_{1-6}$ alkyl or C$_{2-6}$ alkenyl; and
Z is (CR$_{14}$R$_{15}$)$_n$ where n is 0, 1 or 2 and R$_{14}$ and R$_{15}$ are independently selected from hydrogen, C$_{1-6}$ alkyl or C$_{2-6}$ alkenyl.

2. A compound according to claim 1, wherein R$_2$, R$_3$ and R$_4$ are hydrogen.

3. A compound according to claim 1, wherein R$_5$ is hydrogen and R$_6$ is hydrogen or C$_{1-6}$ alkyl.

4. A compound according to claim 1, wherein R$_1$ is hydrogen, methyl, ethyl, propyl or prop-2-enyl.

5. A compound according to claim 1, wherein R$_7$ is hydrogen, methyl or ethyl and R$_8$ is hydrogen or methyl.

6. A compound according to claim 1, wherein R$_9$ is hydrogen or methyl and R$_{10}$ is hydrogen, methyl or phenyl.

7. A compound according to claim 1, wherein n in Z is 1 or 2, R$_{14}$ is hydrogen and R$_{15}$ is hydrogen or methyl.

8. A compound according to claim 1 wherein n in Z is 1.

9. A compound selected from the group consisting of:
11-amino-1,2,3,4-tetrahydro-6H-quinindolin-1-one,
11-amino-3,3-dimethyl-1,2,3,4-tetrahydro-6H-quinindolin-1-one,
(±) 11-amino-3-phenyl-1,2,3,4-tetrahydro-6H-quinindolin-1-one,
11-amino-6-methyl,1,2,3,4-tetrahydro-6H-quinindolin-1-one,
11-amino-6-ethyl-1,2,3,4-tetrahydro-6H-quinindolin-1-one,
11-amino-6-n-propyl-1,2,3,4-tetrahydro-6H-quinindolin-1-one,
11-amino-6-(2-propenyl)-1,2,3,4-tetrahydro-6H-quinindolin-1-one,
11-amino-1,2,3,4-tetrahydro-3,3,6-trimethyl-6H-quinindolin-1-one,
(±) 11-amino-6-methyl-3-phenyl-1,2,3,4-tetrahydro-6H-quinindolin-1-one,
(±) 11-amino-3,6-dimethyl-1,2,3,4-tetrahydro-6H-quinindolin-1-one,
(±) 11-amino-2,6-dimethyl-1,2,3,4-tetrahydro-6H-quinindolin-1-one,
(±) 11-amino-2,6-dimethyl-1,2,3,4-tetrahydro-6H-quinindolin-1-one,
(−) 11-amino-2,6-dimethyl-1,2,3,4-tetrahydro-6H-quinindolin-1-one,
(±) 11-amino-2-ethyl-6-methyl-1,2,3,4-tetrahydro-6H-quinindolin-1-one,
11-amino-1,2,3,4-tetrahydro-2,2,6-trimethyl-6H-quinindolin-1-one,
(±) 11-amino-6-methyl-2-(2-propynyl)-1,2,3,4-tetrahydro-6H-quinindolin-1-one,

29

(±) 11-amino-1,2,3,4-tetrahydro-2,4,6-trimethyl-6H-quinindolin-1-one, 12-amino-7-methyl-cyclohepta[5,6]pyrido[2,3-b]indol-1-one, 10-amino-5-methyl-cyclopenta[5,6]pyrido[2,3-b]indol-1-one, or (±) 12-amino-2,7-dimethyl-cyclohepta[5,6]-pyrido[2,3-b]indol-1-one or a pharmaceutically acceptable salt of any of the foregoing compounds.

10. A compound of formula (VI) or a salt thereof:

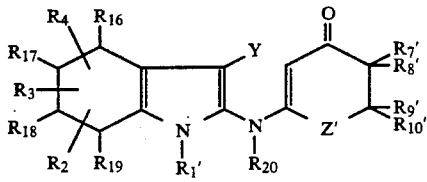

(VI)

wherein Y is a group CN or $COL_1$, where $L_1$ is a leaving group, $R_1'$ is $R_1$ as defined in claim 1 or an N-protecting group, $R_2$, $R_3$, and $R_4$ are as defined in claim 1, $R_7'$, $R_8'$, $R_9'$, and $R_{10}'$ are $R_7$, $R_8$, $R_9$, and $R_{10}$ as defined in claim 1 or a group convertible to $R_7$, $R_8$, $R_9$, and $R_{10}$, respectively, $R_{16}$, $R_{17}$, $R_{18}$, and $R_{19}$ are each hydrogen or $R_{16}$ and $R_{17}$, and $R_{18}$ and $R_{19}$ together represent a bond, $R_{20}$ is hydrogen or an N-protecting group, and Z' is Z as defined in claim 1 or a group convertible thereto.

11. A compound selected from the group consisting of:

1-(4-methoxyphenyl)methyl-2-[(3-oxo-1-cyclohexen-1-yl)amino]-4,5,6,7-tetrahydro-1H-indole-3-carbonitrile, 2-[(5,5-dimethyl-3-oxo-1-cyclohexen-1-yl)amino]-1-(4-methoxyphenyl)methyl-4,5,6,7-tetrahydro-1H-indole-3-carbonitrile, (±) 2-[(5-methyl-3-oxo-1-cyclohexen-1-yl)amino]-1-methyl-1H-indole-3-carbonitrile, (±) 2-[(4-methyl-3-oxo-1-cyclohexen-1-yl)amino]-1-methyl-1H-indole-3-carbonitrile, (±) 2-[(4-ethyl-3-oxo-1-cyclohexen-1-yl)amino]-1-methyl-1H-indole-3-carbonitrile, 2-[(4,4-dimethyl-3-oxo-1-cyclohexen-1-yl)amino]-1-methyl-1H-indole-3-carbonitrile,

30

1-methyl-2-[(3-oxo-1-cyclopenten-1-yl)amino]-1H-indole-3-carbonitrile, 1-methyl-2-[(3-oxo-1-cyclohepten-1-yl)amino]-1H-indole-3-carbonitrile, or 1-methyl-2-[(3-oxo-1-cyclohexen-1-yl)amino]-1H-indole-3-carbonitrile.

12. A compound of formula (VII) of a salt thereof:

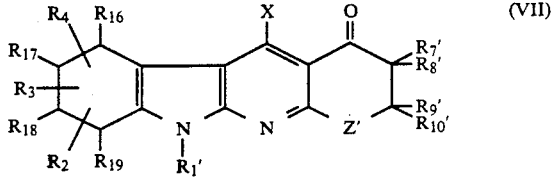

(VII)

wherein X is $NH_2$, OH or chloro, $R_1'$, $R_2$, $R_3$, $R_4$, $R_7'$, $R_8'$, $R_9'$, $R_{10}'$, $R_{16}$, $R_{17}$, $R_{18}$, $R_{19}$, are as defined in claim 10 and Z' is Z as defined in claim 1 or a group convertible to Z, with the proviso that when $R_1'$, $R_7'$, $R_8'$, $R_9'$, $R_{10}'$, and Z' are $R_1$, $R_7$, $R_8$, $R_9$, $R_{10}$ and Z as defined in claim 10 and $R_{16}$ and $R_{17}$, and $R_{18}$ and $R_{19}$ together represent a bond, X is not $NH_2$.

13. A compound selected from the group consisting of:

11-amino-6-(4-methoxyphenyl)methyl-1,2,3,4,7,8,9,10-octahydro-6H-quinindolin-1-one, 11-amino-3,3-dimethyl-6-(4-methoxyphenyl)methyl-1,2,3,4,7,8,9,10-octahydro-6H-quinindolin-1-one, (±) 11-amino-6-(4-methoxyphenyl)methyl-1,2,3,4,7,8,9,10-octahydro-3-phenyl-6H-quinindolin-1-one, 11-amino-6-(4-methoxyphenyl)methyl-1,2,3,4-tetrahydro-6H-quinindolin-1-one, 11-amino-3,3-dimethyl-6-(4-methoxyphenyl)methyl-1,2,3,4-tetrahydro-6H-quinindolin-1-one or (±) 11-amino-6-(4-methoxyphenyl)methyl-3-phenyl-1,2,3,4-tetrahydro-6H-quinindolin-1-one.

14. A pharmaceutical composition for use in treating anxiety or depression in mammals comprising a therapeutically effective amount of a compound according to claim 1 and a pharmaceutically acceptable carrier.

15. A method of treatment of anxiety or depression in mammals, which comprises administering to the sufferer a therapeutically effective amount of a compound according to claim 1.

* * * * *